(12) United States Patent
Goto

(10) Patent No.: US 8,423,128 B2
(45) Date of Patent: Apr. 16, 2013

(54) CARDIAC ARREST MONITORING DEVICE

(75) Inventor: Hiroshi Goto, Ibaraki (JP)

(73) Assignee: Empire Technology Development LLC, Wilmington, DE (US)

( * ) Notice: Subject to any disclaimer, the term of this patent is extended or adjusted under 35 U.S.C. 154(b) by 16 days.

(21) Appl. No.: 12/645,309

(22) Filed: Dec. 22, 2009

(65) Prior Publication Data

US 2011/0152702 A1 Jun. 23, 2011

(51) Int. Cl.
*A61B 5/04* (2006.01)
(52) U.S. Cl.
USPC ............ 600/522; 600/509; 600/513; 600/523
(58) Field of Classification Search .................. 600/509, 600/513, 522, 523
See application file for complete search history.

(56) References Cited

U.S. PATENT DOCUMENTS

| 6,292,687 | B1 * | 9/2001 | Lowell et al. ................ 600/515 |
| 6,493,581 | B2 * | 12/2002 | Russell ............................. 607/5 |
| 6,985,771 | B2 * | 1/2006 | Fischell et al. ................... 607/3 |
| 2005/0065445 | A1 * | 3/2005 | Arzbaecher et al. .......... 600/515 |

FOREIGN PATENT DOCUMENTS

| JP | 2001-327472 | 11/2001 |
| JP | 2004-129980 | 4/2004 |
| JP | 2009-224967 | 10/2009 |
| JP | 2011-066861 | 3/2011 |
| WO | WO03/082102 | 10/2003 |
| WO | 2008149467 A1 | 12/2008 |

* cited by examiner

*Primary Examiner* — Christopher D. Koharski
*Assistant Examiner* — Natasha Patel

(57) ABSTRACT

The embodiments herein relate to devices, implementations, and techniques for health monitoring, specifically cardiac arrest monitoring systems. A paramedical equipment locator may receive a periodically sent message configured to identify a location information corresponding to a paramedical equipment and determine whether to select the paramedical equipment based at least in part on the location information.

10 Claims, 11 Drawing Sheets

CARDIAC ARREST MONITORING DEVICE

BACKGROUND

Unless otherwise indicated herein, the approaches described in this section are not prior art to the claims in this application and are not admitted to be prior art by inclusion in this section.

An effective way to treat cardiac arrest may be with a defibrillator. A defibrillator is a medical device that delivers an electric current, or "shock" to the chest of a cardiac arrest victim, which delivers that electric current to the victim's heart. The shock can interrupt the erratic electrical pulse of ventricular fibrillation of the heart during the cardiac arrest, which can give the victim's heart a chance to begin beating at its normal rhythm.

During the first 10 minutes after a person suffers a cardiac arrest, every minute saved before defibrillation may mean about a 10 percent increase in relative survival rate. Therefore, as time is critical, there has been an increase in the availability of automated external defibrillators, or AEDs. AEDs are portable medical devices designed primarily for use by "first responders" (first to arrive at the scene of a medical emergency), such as police and fire departments. An AED generally has a built-in computer that evaluates a victim's heat rhythm to determine whether a shock is required. AEDs are also relatively easy to use as they typically include voice instructions and screen messages to assist in its operation, and thus, can be used by an average citizen with little or no training.

As the AEDs have become more simple to use, they are being installed in a variety of public and private settings, including but not limited to, schools, sports facilities, transportation hubs, office buildings, elder care facilities, government buildings, and the like.

BRIEF DESCRIPTION OF THE DRAWINGS

The subject matter of the present disclosure is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

Figure 1:
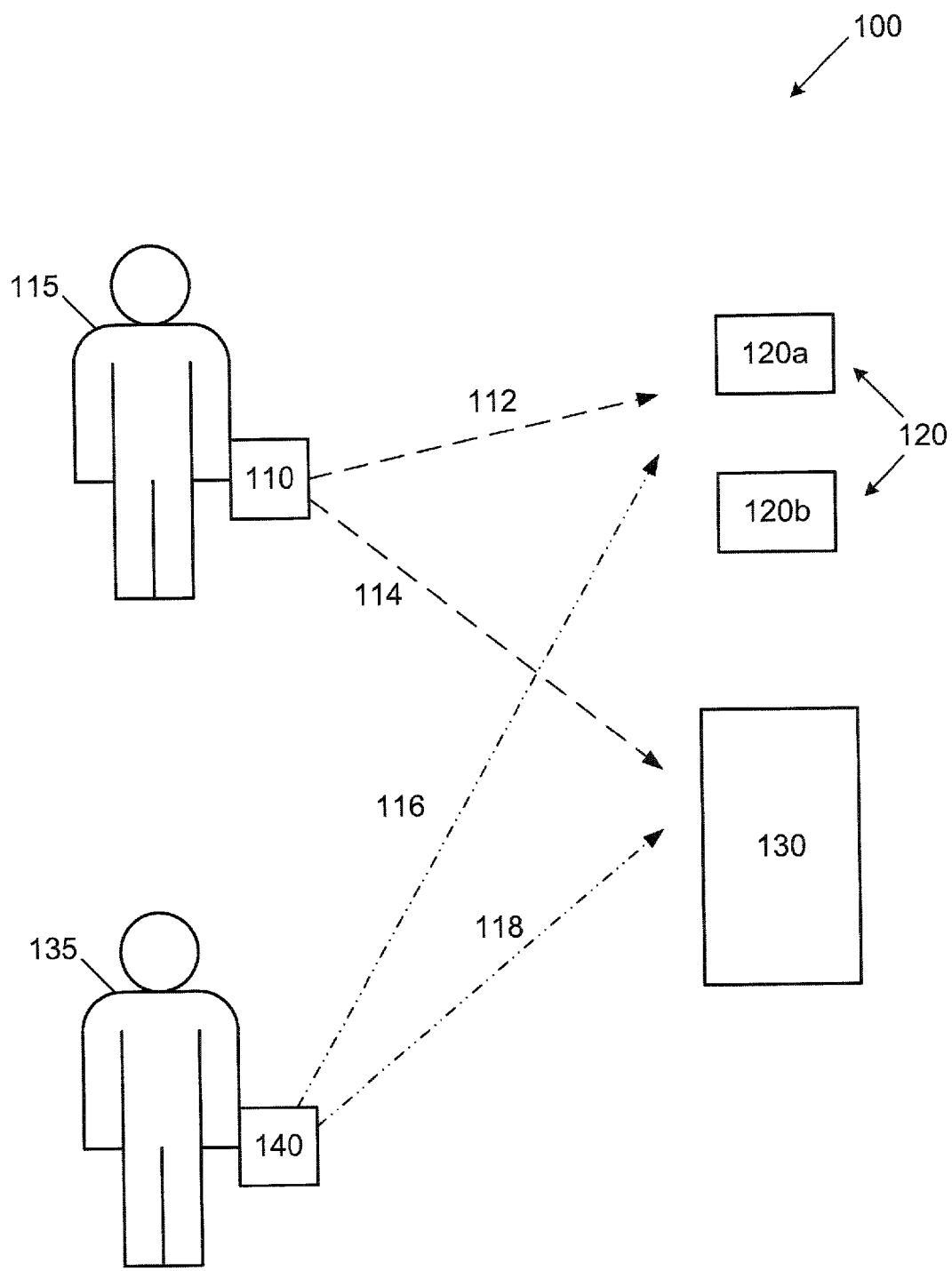
FIG. 1 illustrates a cardiac arrest monitoring system, according to one embodiment of the present disclosure.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, systems, and/or computer program products related to health monitoring, such as a cardiac arrest monitoring systems.

The subject matter described herein provides a cardiac arrest monitoring system, which may included:

a. Cardiac Arrest Monitoring Device, which monitors a user's cardiac rhythm, detects anomalies, locates nearby paramedical equipment, and outputs the location information of the paramedical equipment. This device may generate an audio and/or visual alarm to notify passersby of the cardiac victim/user's distress;

b. Paramedical Device, connected to paramedical equipment, such as automated external defibrillator (hereinafter "AED"), which may be configured to output the location information of a patient who wears the cardiac arrest monitoring device. Further, this device may be configured to generate an audio and/or visual alarm to notify passersby of the existence of a victim/user who needs the paramedical equipment connected to the paramedical device; and c. Mobile Terminal Device, which is for use by a passerby who encounters a victim of a cardiac arrest. The mobile terminal device searches nearby paramedical equipment and outputs the location information of the paramedical equipment to the passerby.

Referring to FIG. 1, one embodiment of a cardiac arrest monitoring system 100 may include a cardiac arrest monitoring device 110, which may be worn by a patient/user 115. The cardiac arrest monitoring device 110 may communicate with at least one paramedical device (illustrated as 120a and 120b). Although illustrated as 120a and 120b, the paramedical devices will be referred to collectively as 120, as there may be any number of paramedical devices. The communication with the paramedical devices 120 may be wireless as illustrated by wireless communication line 112. The cardiac arrest monitoring device 110 may communicate with a server 130, which contains the location information of the paramedical devices 120a and 120b. The communication with the server 130 may be wireless, as illustrated by wireless communication line 114. The cardiac arrest monitoring system 100 may also include a mobile terminal device 140 which may be carried by a user 135. The mobile terminal device 140 may communicate with at least one paramedical device 120. The communication may be wireless, as illustrated by wireless communication line 116. The mobile terminal device 140 may communicate with the server 130, which contains the location information of the paramedical devices 120a and 120b. The communication with the paramedical devices 120 may be wireless, as illustrated by wireless communication line 118.

Thus, when an anomaly in a cardiac rhythm is detected by the cardiac arrest monitoring device 110, the device searches for nearby paramedical equipment 120 (either through a server 130 or the paramedical equipment 120 itself), and outputs the location information of the paramedical equipment 120.

Figure 2:
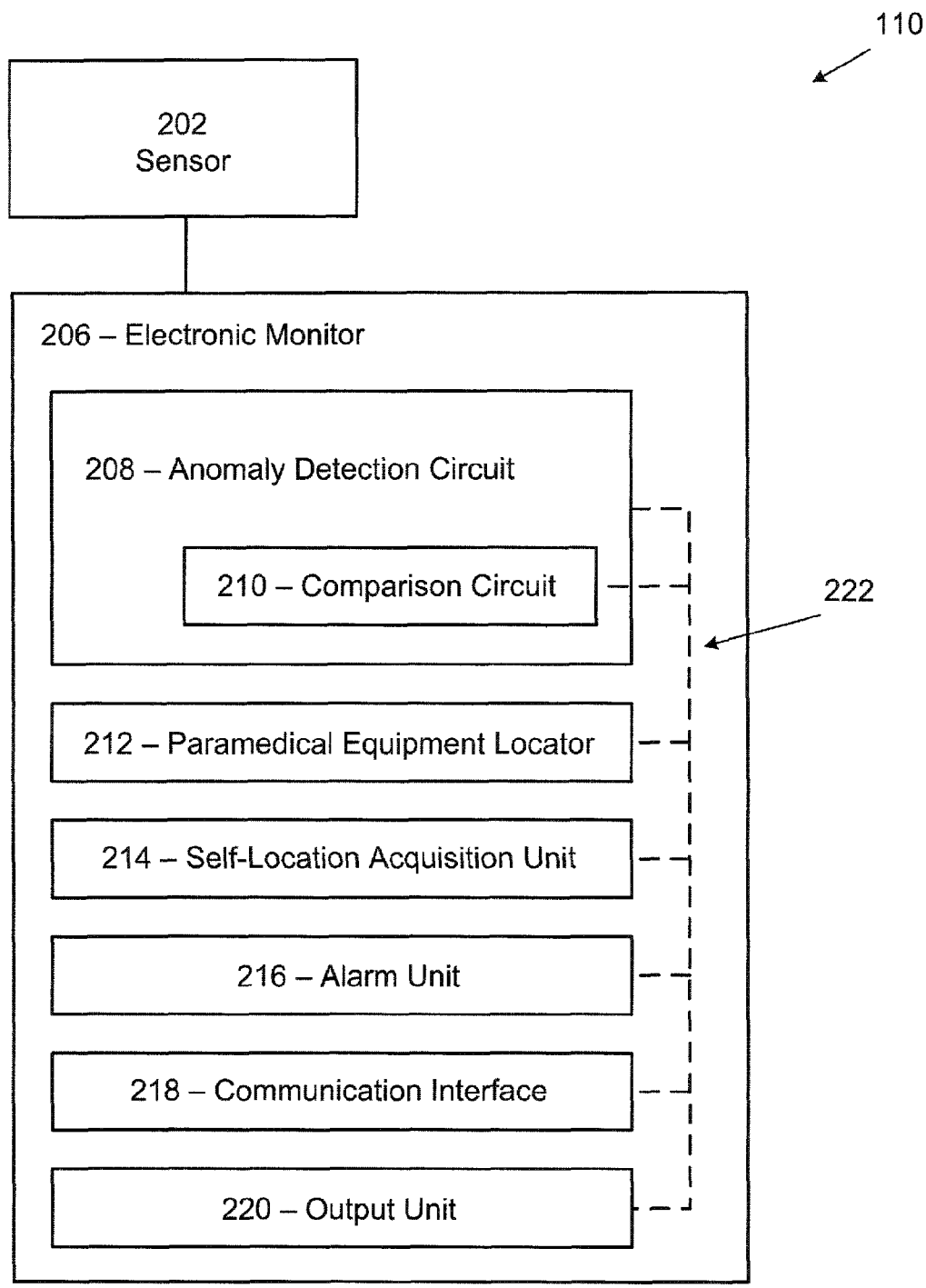
FIG. 2 illustrates a cardiac arrest monitoring device, according to one embodiment of the present disclosure.

Referring to FIGS. 1 and 2, one embodiment of the cardiac arrest monitoring device 110 of FIG. 1 may include an electronic monitor 206 coupled to a sensor 202. The electronic monitor 206 monitors the cardiac rhythm of the patient/user 115 through the sensor 202, which may be adapted to attach to the patient/user 115. The sensor 202 may be adapted to detect a user's cardiac rhythm and store such data continuously as an electrical signal, such as an electrocardiograph or ECG, as will be understood to those skilled in the art.

The electronic monitor 206 may include an anomaly detection circuit 208. The anomaly detection circuit 208 may comprise a logic circuit that analyzes data received from the sensor 202 to detect anomalies in cardiac rhythm. The anomaly detection circuit 208 may include a comparison circuit 210. The comparison circuit 210 may be adapted to compare the received cardiac rhythm data by the anomaly detection circuit 208 with preprogrammed data. The examples of "preprogrammed data" may included, but is not limited to, previous data of the user, average populous data (e.g. 60-100 beats per minute), average data of a specific demographic (age, sex, location, etc.), and the like. The anomaly detection circuit 208 in conjunction with its comparison circuit 210 may determine whether an anomaly of cardiac rhythm is occurring, e.g., a lack of a heartbeat for a certain period or a substantial difference from the preprogrammed data.

The electronic monitor 206 may further include a paramedical equipment locator 212. The paramedical equipment locator 212 may be adapted to identify the location of the paramedical device 120. The paramedical equipment locator 212 may wirelessly broadcast a message to request the location information of the paramedical device 120, and may receive the location information from the paramedical device 120 itself, as will be discussed. In response to receiving the location information, the paramedical equipment locator 212 may select one or more nearby paramedical devices 120 by calculating the distance between the cardiac arrest monitoring device 110 and each paramedical device 120. Alternately, the paramedical device 120 may broadcast its location information periodically, regardless whether or not the cardiac arrest monitoring device 110 requests the location information, as will be discussed. Thus, the cardiac arrest monitoring device 110 can receive the location information for each paramedical device 120, without sending a request of the location information.

Referring to FIGS. 1 and 2, in another embodiment, the cardiac arrest monitoring device 110 through its paramedical equipment locator 212 may request the location information for the paramedical device 120 from the server 130, which may manage the location information of paramedical device 120. The cardiac arrest monitoring device 110 may also send the server 130 its location information to obtain the location information for nearby paramedical device 120. A self-location acquisition unit 214 such as a GPS receiver may be coupled or installed in the cardiac arrest monitoring device 110, which can determine the location of the cardiac arrest monitoring device 110 or a user 115 (victim). The paramedical equipment locator 212 may use this location information to calculate the distance between a user (i.e., the cardiac arrest monitoring device 110) and the paramedical device 120.

The electronic monitor 206 may also have an alarm unit 216. The alarm unit 216 may generate an alarm, e.g. audible and/or visual, to notify a passerby of a cardiac anomaly that is occurring with the patient/user 115, in responding to the anomaly detection circuit 208 detecting the anomaly in the cardiac rhythm.

The electronic monitor 206 may further include a communication interface 218. The communication interface 218 may control the communication between the electronic monitor 206 and the paramedical device 120 and/or the server 130. The communication interface 218 may include, but is not limited to, a wireless communication device.

Figure 3:
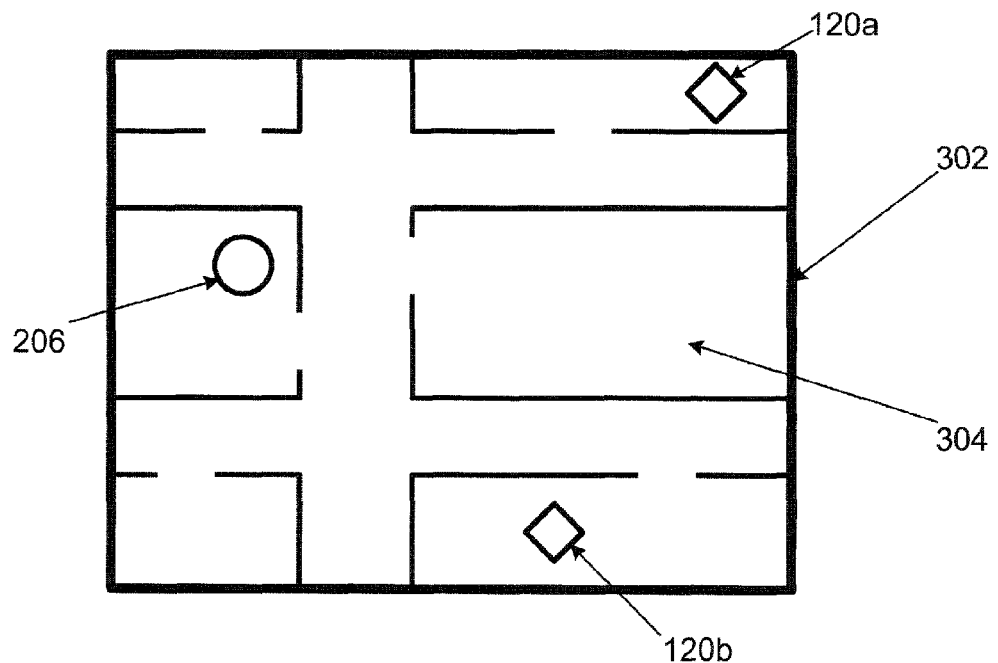
FIG. 3 illustrates a map displayed on a monitor, according to one embodiment of the present disclosure.
Figure 4:
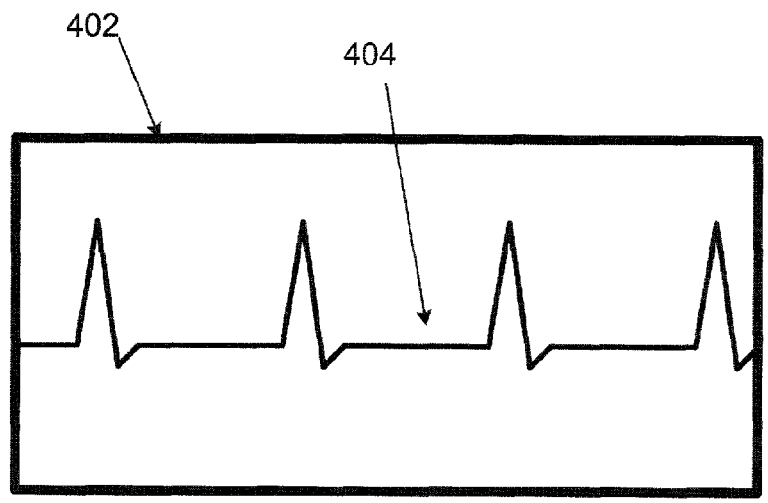
FIG. 4 illustrates a cardiac rhythm on a monitor, according to one embodiment of the present disclosure.

The electronic monitor 206 may also have an output unit 220. The output unit 220 may be, for example, a video display, audio speaker, and the like. The output unit 220 may output information of the location of the paramedical device 120. For example, as shown in FIG. 3, the location of the electronic monitor 206 (e.g. location of the user 115) and the location of nearby paramedical devices 120a and 120b may be displayed on a map 304 on a video display or monitor 302. Furthermore, as shown in FIG. 4, the output unit 220 may graphically display the detected cardiac rhythm data/inter-pulse time 404 on a video display or monitor 402.

Referring again to FIG. 2, it is understood that components, such as 208, 212, 214, 216, 218, and 220 may be in communication with one and other through a bus 222. It is also understood that the term "bus", as used within this detailed description, may refer to any communication coupling method between the various components, including but not limited to wired communication and wireless communication.

Figure 5:
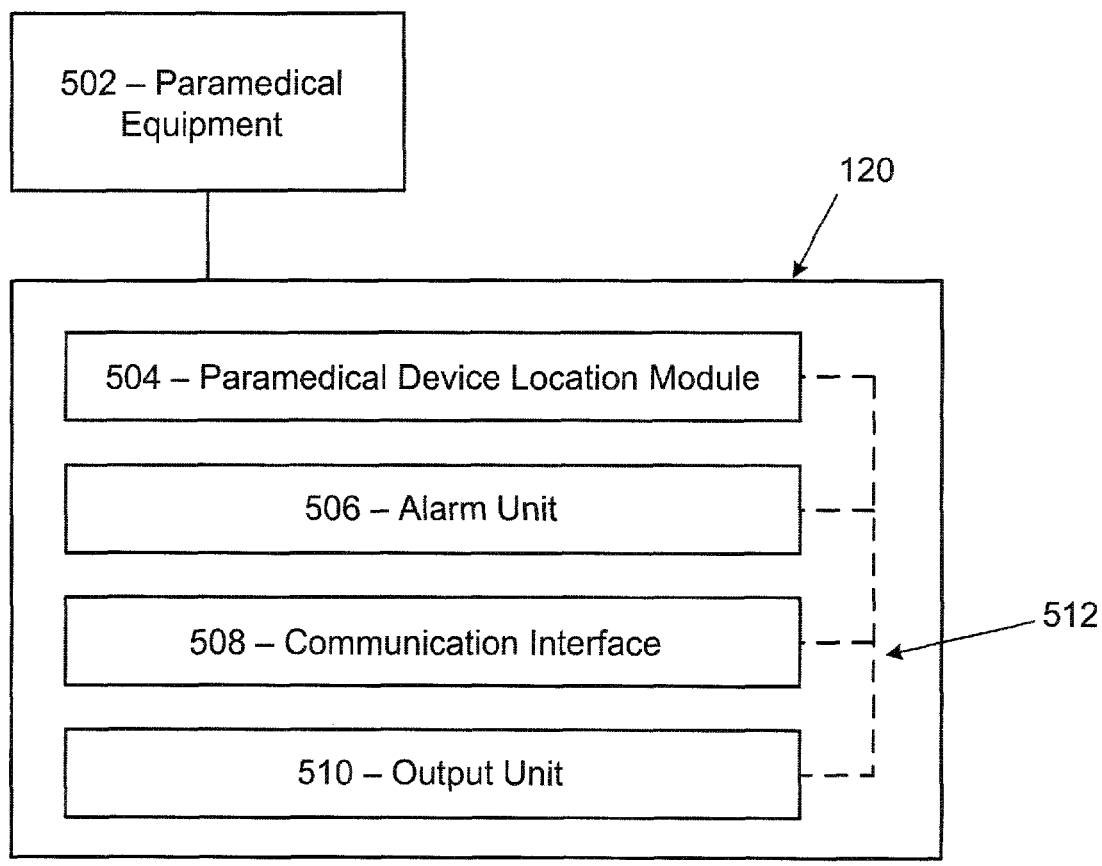
FIG. 5 illustrates a paramedical device, according to one embodiment of the present disclosure.

As previously discussed, the present disclosure may include a paramedical device 120, as shown in FIG. 1. As shown in FIG. 5, the paramedical device 120 may connected to an article of paramedical equipment 502, such as an AED. The paramedical device 120 may send its location information to the cardiac arrest monitoring device 110, as shown in FIG. 1. The paramedical device 120 may also be configured to output the location information of a victim, e.g. user 115, who wears the cardiac arrest monitoring device 110, and generate an alarm to notify passersby of existence of a victim who need this paramedical equipment 502, e.g. the AED.

Referring to FIGS. 1 and 5, one embodiment of the paramedical device 120 may include a paramedical device location module 504. The paramedical device location module 504 may provide the cardiac arrest monitoring device 110 with the location information of the paramedical equipment 502 to which the paramedical device 120 is attached. The paramedical device location module 504 may send such information in responding to receiving a request from the cardiac arrest monitoring device 110. Alternately, the paramedical device location module 504 may broadcast the location information periodically, regardless whether or not the cardiac arrest monitoring device 110 requests the location information. The paramedical device location module 504 may include a memory module (such as a non-volatile flash module), which may store the location information or may be a self-location acquisition unit such as a GPS receiver to obtain its location information.

The paramedical device 120 may also have an alarm unit 506. The alarm unit 506 may generate an alarm, e.g. audible and/or visual, to notify a passerby of a cardiac anomaly that is occurring with the user, in responding to receiving the location information of the cardiac arrest monitoring device 110 (e.g. the location of the victim).

The paramedical device 120 may further include a communication interface 508. The communication interface 508 may facilitate the communication between the paramedical device 120 and the cardiac arrest monitoring device 110 and/or the server 130. The communication interface 508 may include, but is not limited to, a wireless communication device.

The paramedical device 120 may also have an output unit 510. The output unit 510 may be, for example, a video display, audio speaker, and the like. The output unit 510 may output information of the location of a victim (e.g. user 115) who wears the cardiac arrest monitoring device 110. For example, the location of the victim may displayed on a map 304 on the monitor 302, which can show the location of an electronic monitor 206 (e.g. location of the user 115) and the location of nearby paramedical devices 120*a* and 120*b*, such as shown in FIG. 3.

Referring again to FIG. 5, it is understood that components, such as 504, 506, 508, and 510 may be in communication with one and other through a bus 512.

As previously discussed, another embodiment of the present disclosure may include the mobile terminal device 140. The mobile terminal device 140 may be used by a passerby, e.g. user 135 (such as a care worker), who may encounter a victim (e.g. user 115) of cardiac arrest. The mobile terminal device 140 may search for nearby paramedical devices 120 and may output the location information of the paramedical device 120.

Figure 6:
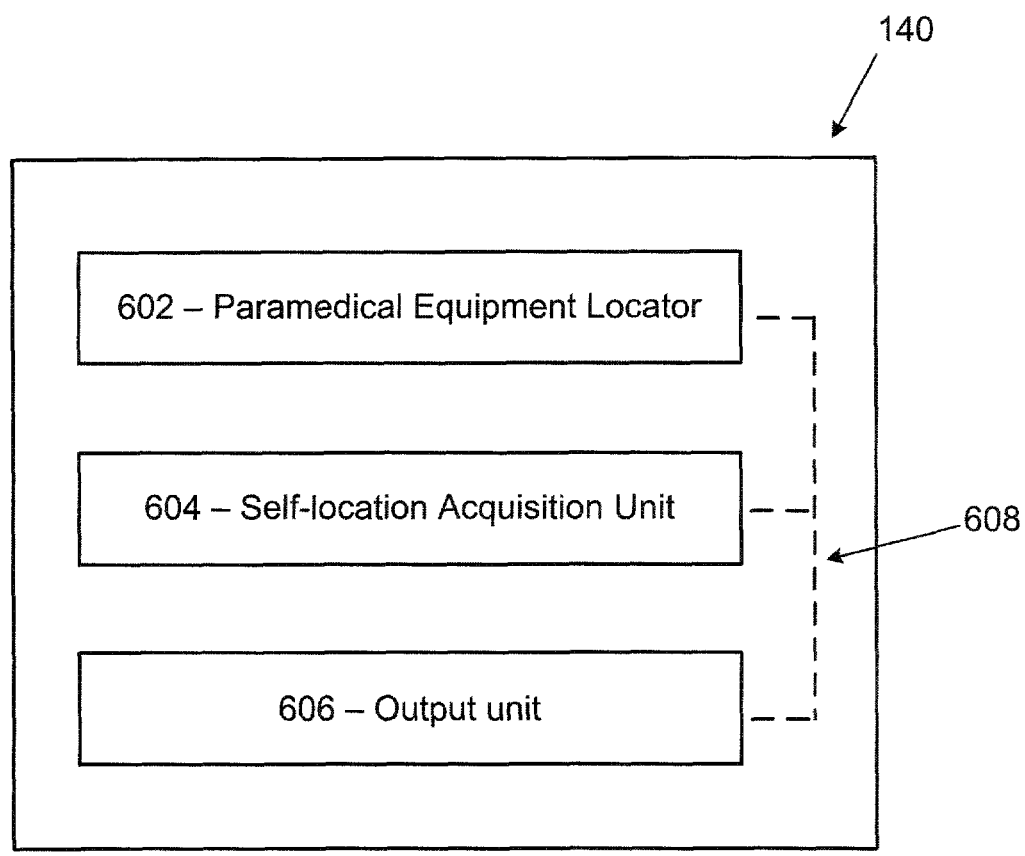
FIG. 6 illustrates a mobile terminal device, according to one embodiment of the present disclosure.

As shown in FIGS. 1 and 6, the mobile terminal device 140 may include a paramedical equipment locator 602. The paramedical equipment locator 602 may broadcast or send message to request the location information of the paramedical device 120, and may receive the location information from the paramedical device 120. Upon receiving the location information of the paramedical device 120, the paramedical equipment locator 602 may select one or more nearby paramedical device 120*a* and 120*b* by determining a distance between the mobile terminal device 140 and the paramedical device 120. In another embodiment, the paramedical equipment locator 602 may request a location information for the paramedical device 120 from the server 130, which may manage the location information of the paramedical devices 120. The mobile terminal device 140 may send the server 130 its location information, and in turn, the server 130 may provide the location information of nearby paramedical devices 120. To determine its location the mobile terminal device 140 may include a self-location acquisition unit 604, such as a GPS receiver.

The mobile terminal device 140 may also have an output unit 606. The output unit 606 may be, for example, a video display, audio speaker, and the like. The output unit 606 may output information of the location of the nearest paramedical devices 120. For example, the location of the victim (e.g. user 115) may be displayed on a map 304 on the monitor 302, which may show the location of nearby paramedical devices 120, such as shown in FIG. 3.

Referring again to FIG. 6, it is understood that components, such as 602, 604, and 606 may be in communication with one and other through a bus 608.

FIGS. 7-10 show examples of process flows in accordance with at least some embodiments of the present disclosure. The processes described herein, set forth various functional blocks or actions that may be described as process flows, functional operations, events and/or acts, etc., which may be performed by hardware, software, and/or firmware. Those skilled in the art, in light of the present disclosure, will recognize that numerous alternatives to the functional blocks shown in FIGS. 7-10 may be practiced in various implementations. For example, although the processes, as shown in FIGS. 7-10, comprise one particular order of blocks or actions, the order in which these blocks or actions are presented does not necessarily limit claimed subject matter to any particular order. Likewise, intervening actions not shown in FIGS. 7-10 and/or additional actions not shown in FIG. 7-10 may be employed and/or some of the actions shown in FIGS. 7-10 may be eliminated, without departing from the scope of claimed subject matter.

Figure 7:
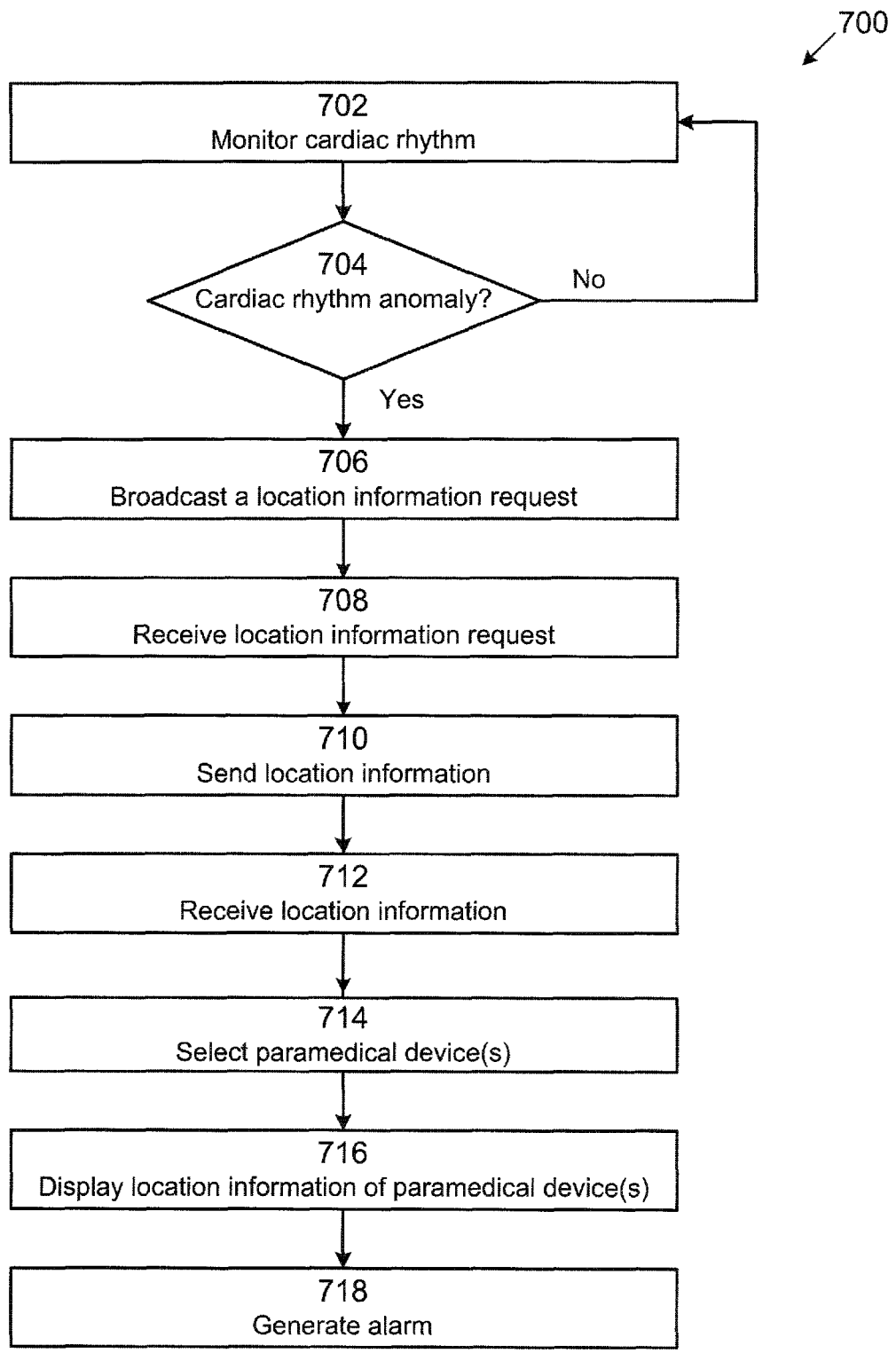
FIGS. 7-10 are block diagrams illustrating process flows for the cardiac arrest monitoring system, according to one embodiment of the present disclosure.

The process 700 illustrates the operation of a cardiac arrest monitoring device, which receives a location information of paramedical equipment (e.g. an AED) from one or more paramedical devices to which the paramedical equipment is attached, and responsive to the received location information, communicates the location information for a paramedical equipment. Referring to FIG. 7, a cardiac rhythm may be monitored with a sensor 202, at block 702. At block 704, the cardiac rhythm data may be analyzed. If an anomaly detection circuit 208 analyzes data received from the sensor 202 to detect anomaly of cardiac rhythm. The anomaly detection circuit 208 decides anomaly of cardiac rhythm on condition that it detects no beat in a certain period or substantial difference from the preprogrammed data. If anomaly is detected, the process moves to block 706. If no anomaly is detected, the process moves back to block 702. Block 706 may represent broadcasting a location information request for paramedical equipment upon detection of an anomaly. Block 708 may represent a paramedical device 120 receiving the broadcasted request from block 706. Block 710 may represent the paramedical device 120 sending the location information for the paramedical equipment (e.g. the AED) back to the cardiac arrest monitoring device 110. Block 712 may represent the cardiac arrest monitoring device receiving the location information of the paramedical equipment. Block 714 may represent the cardiac arrest monitoring device selecting one or more nearby paramedical equipment by calculating the distance between the cardiac arrest monitoring device 110 and each piece of paramedical equipment. Block 716 may represent communicating information regarding the location of nearby paramedical equipment, such a displaying the location on a map. Block 718 may represent generating an alarm to notify passersby of anomaly of the user, in responding to the anomaly detection circuit detecting the anomaly of the cardiac rhythm. It is, of course, understood that block 718 may occur at any point in the process after block 704 detects an anomaly.

Figure 8:
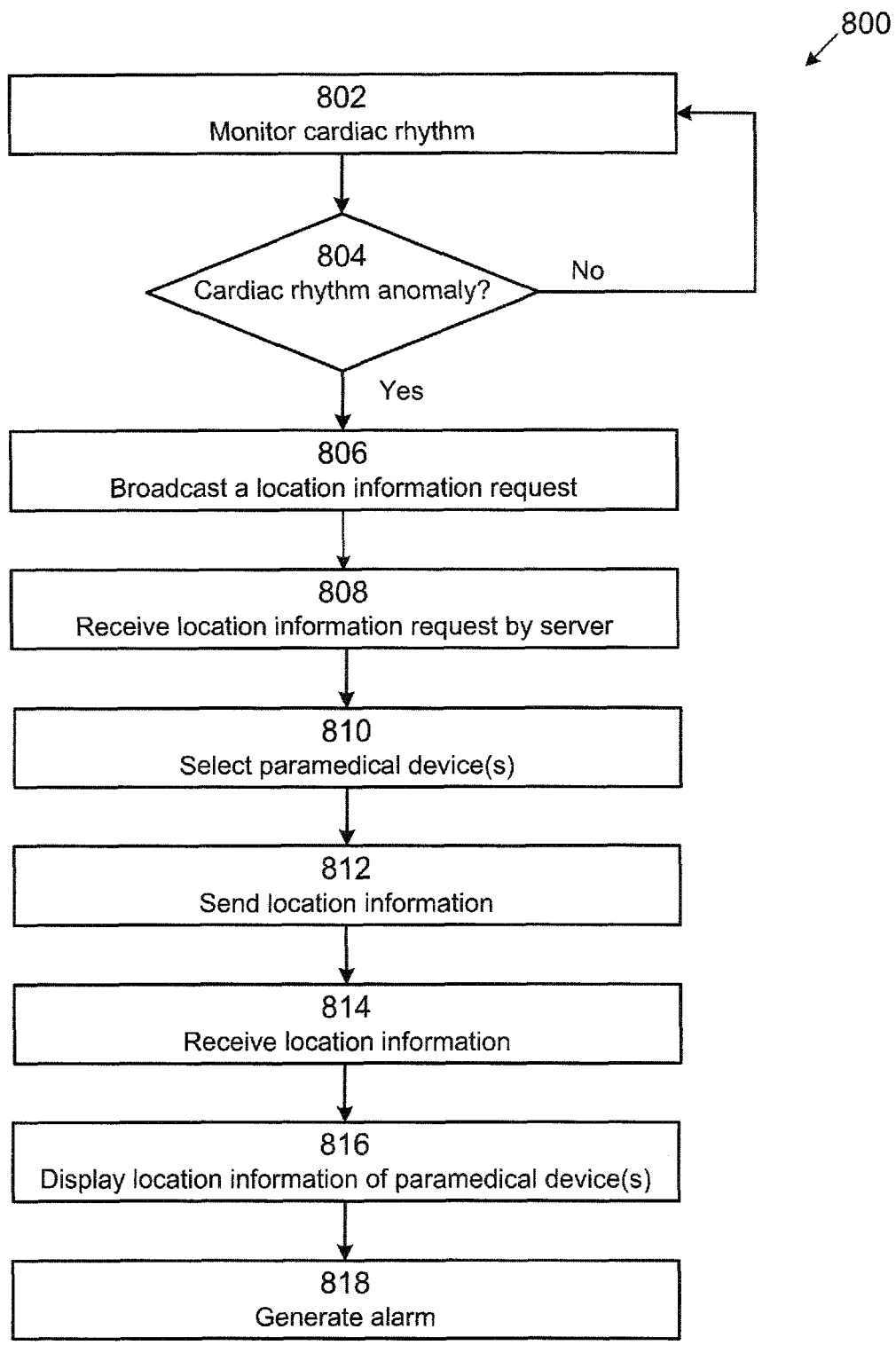

The process 800 illustrates the operation of a cardiac arrest monitoring device, which receives the location information of the paramedical equipment from a server, which manages the location information of the paramedical equipment, and communicates the location information. Referring to FIG. 8, block 802 may comprise monitoring a cardiac rhythm with a sensor 202. Block 804 may represent analyzing the cardiac rhythm data. If an anomaly detection circuit 208 analyzes data received from the sensor 202 to detect anomaly of cardiac rhythm. The anomaly detection circuit 208 decides anomaly of cardiac rhythm on condition that it detects no beat in a certain period or substantial difference from the preprogrammed data. If anomaly is detected, the process moves to block 806. If no anomaly is detected, the process moves back to block 802. Block 806 may represent broadcasting a local information request for paramedical equipment and self-location information to a server upon detection of an anomaly. Block 808 may represent a server 130 receiving the broadcasted request from block 806. Block 810 may represent the server selecting one or more paramedical devices based on the location information of the cardiac arrest monitoring device. Block 812 may represent the server sending the location information of paramedical equipment back to the cardiac arrest monitoring device. Block 814 may represent the cardiac arrest monitoring device receiving the location information of the paramedical equipment. Block 816 may represent communicating information regarding the location of nearby paramedical equipment, such a displaying the location on a map. Block 818 may represent generating an alarm to notify passersby of anomaly of the user, in responding to the anomaly detection circuit detecting the anomaly of the cardiac rhythm. It is, of course, understood that block 818 may occur at any point in the process after block 804 detects an anomaly.

Figure 9:
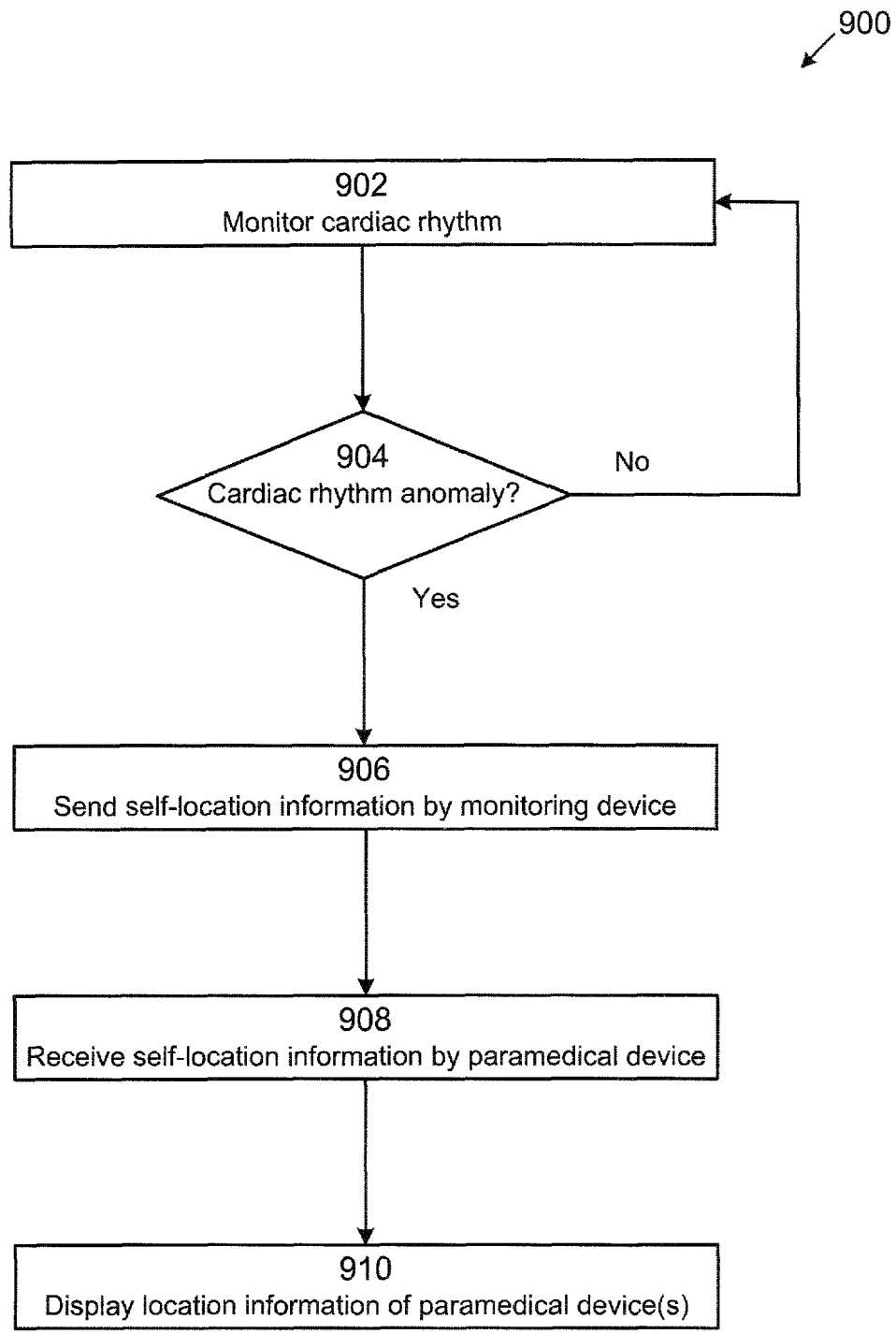

The process 900 illustrates the operation of a paramedical device, which communicates the location information of a victim (e.g. user 115), when the paramedical device receives the location information of a victim from the cardiac arrest monitoring device worn by the victim. Referring to FIGS. 2 and 9, block 902 may comprise monitoring a cardiac rhythm with a sensor 202. Block 904 may represent analyzing the cardiac rhythm data. If an anomaly detection circuit 208 analyzes data received from the sensor 202 to detect anomaly of cardiac rhythm. The anomaly detection circuit 208 decides anomaly of cardiac rhythm on condition that it detects no beat in a certain period or substantial difference from the preprogrammed data. If anomaly is detected, the process moves to block 906. If no anomaly is detected, the process moves back to block 902. Block 906 may represent the cardiac arrest monitoring device sending self-location information to the paramedical device upon detection of an anomaly. Block 908 may represent the paramedical device receiving the location information of the victim (i.e. the cardiac monitoring device). Block 910 may represent communicating information regarding the location of the victim, such a displaying the location on a map.

Figure 10:
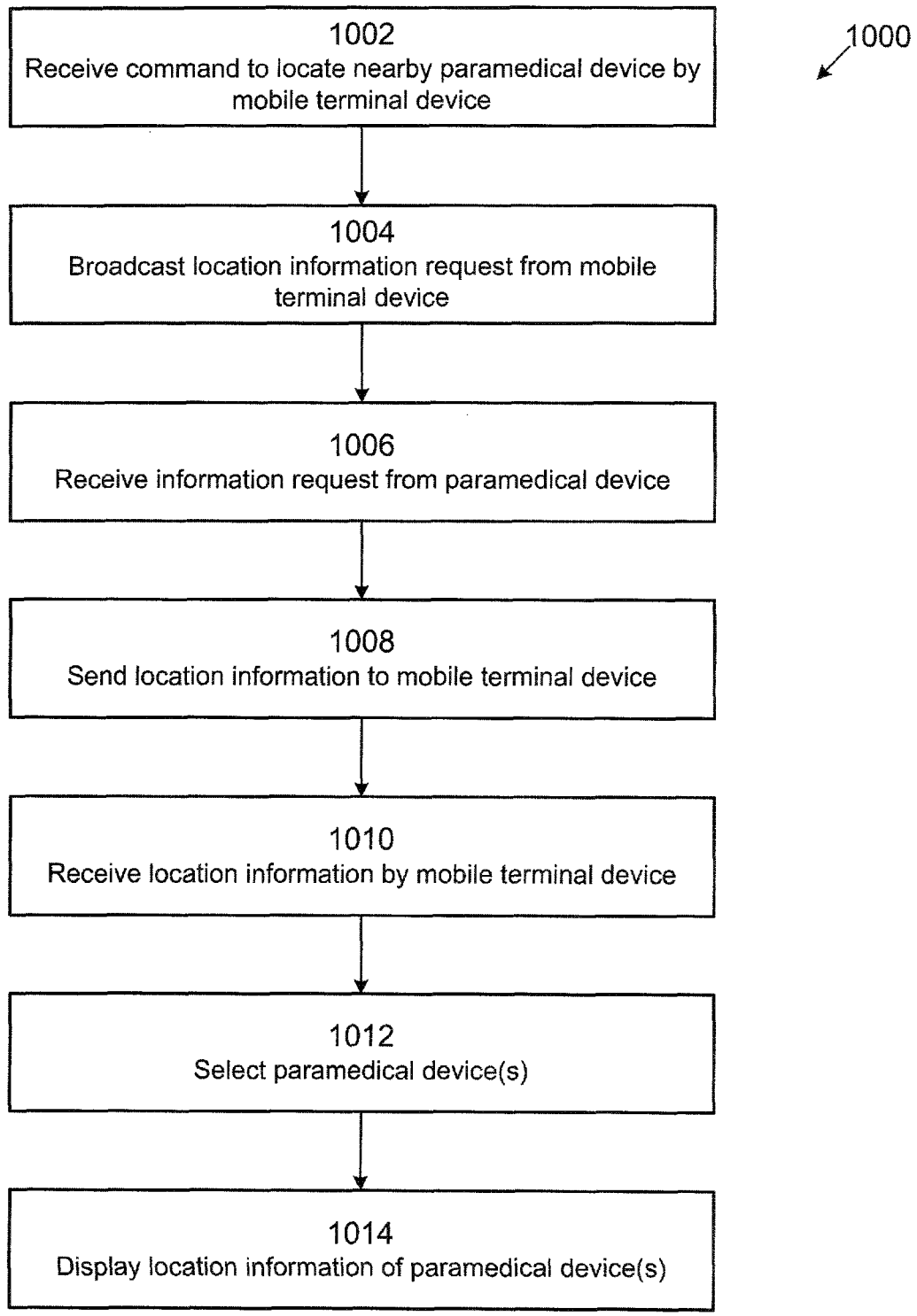

The process 1000 illustrates the operation of a mobile terminal device, which receives the location information of paramedical equipment from one or more paramedical devices to which the paramedical equipment is attached, and communicates the location information for the paramedical equipment. This device is for the use of passersby who encounter a victim of cardiac arrest. Referring to FIG. 10, block 1002 may represent receiving a command to locate a nearby article of paramedical equipment, such as by a user who inputs a command on the mobile terminal device to locate nearby paramedical equipment. Block 1004 may represent broadcasting a local information request for paramedical equipment. Block 1006 may represent a paramedical device receiving the broadcasted request from block 1004. Block 1008 may represent the paramedical device sending the location information of the paramedical equipment back to the mobile terminal device. As previously discussed, the location information of paramedical equipment may be stored in the memory of the paramedical device. In another embodiment, the paramedical device may include a self-location acquisition unit such as a GPS receiver to obtain its location information. Block 1010 may represent the mobile terminal device receiving the location information of the paramedical equipment. Block 1012 may represent the mobile terminal device selecting one or more nearby paramedical equipment by calculating the distance between the cardiac arrest monitoring device and each of the pieces of paramedical equipment. Block 1014 may represent communicating information regarding the location of nearby paramedical equipment, such a displaying the location on a map.

It is, of course, understood that the mobile terminal device may receive the location information of the paramedical equipment from a server, which manages the location information of the paramedical equipment, as discussed with regard to FIG. 8.

Figure 11:
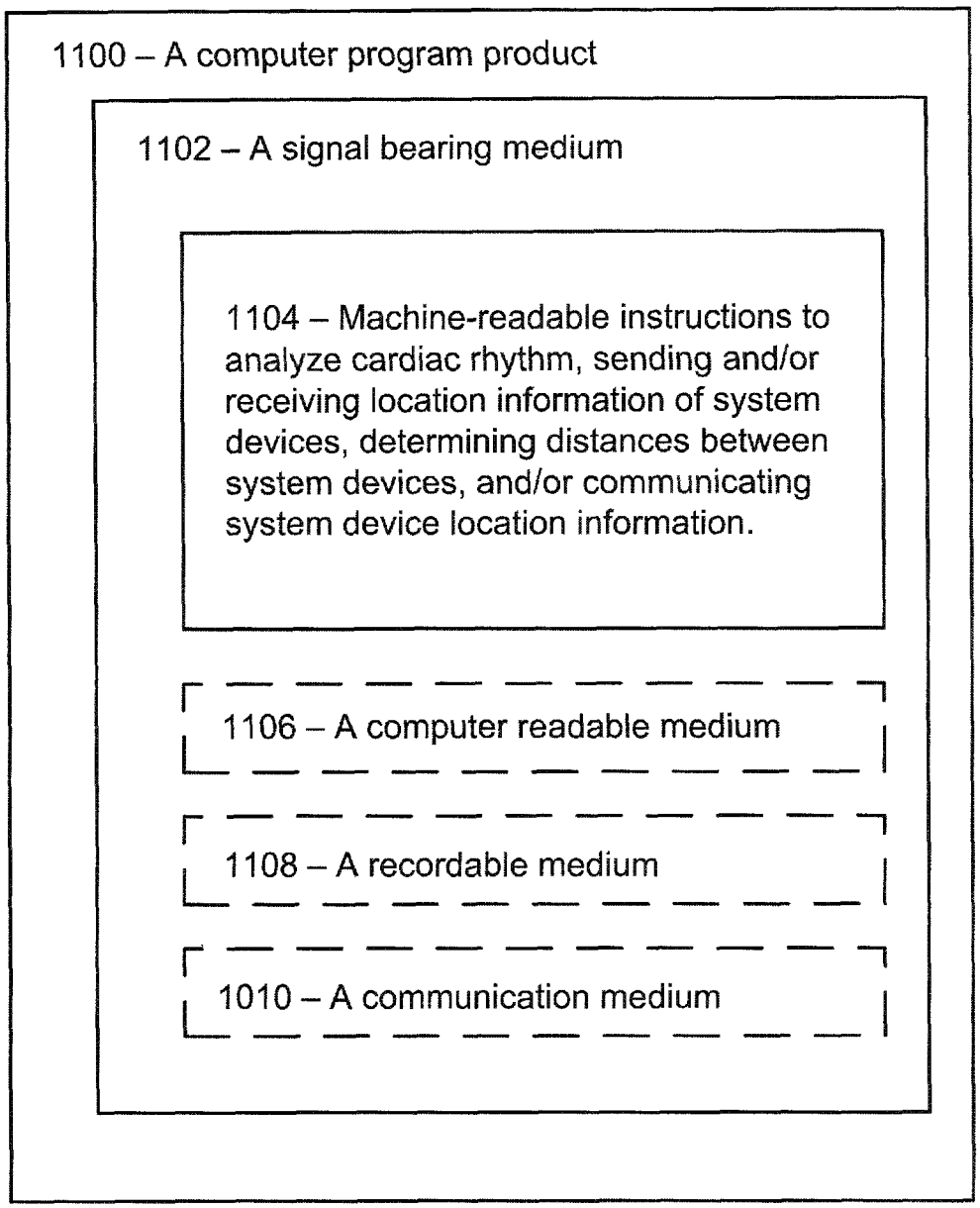
FIG. 11 is a schematic illustrating an example computer program product that is arranged in accordance with the present disclosure.

FIG. 11 illustrates an example computer program product 1100 that is arranged in accordance with the present disclosure. Computer program product 1100 may include a signal bearing medium 1102. Signal bearing medium 1102 may include one or more machine-readable instructions 1104, which, if executed by one or more processors, may operatively enable a computing device to provide the functionality described above with respect to FIGS. 7-10; in specific, analyzing cardiac rhythm, sending and/or receiving location information of system devices, and/or communication system device location information. Thus, for example, referring to FIG. 1, cardiac arrest monitoring device 110, paramedical device 120, and/or server 130, and/or mobile terminal device 140 may undertake one or more of the actions shown in FIGS. 7-10 in response to instructions 1104 conveyed by medium 1102.

In some implementations, signal bearing medium 1102 may encompass a computer-readable medium 1106, such as, but not limited to, a hard disk drive, a Compact Disc (CD), a Digital Versatile Disk (DVD), a digital tape, memory, etc. In some implementations, signal bearing medium 1102 may encompass a recordable medium 1108, such as, but not limited to, memory, read/write (R/W) CDs, R/W DVDs, etc. In some implementations, signal bearing medium 1102 may encompass a communications medium 1110, such as, but not limited to, a digital and/or an analog communication medium (e.g., a fiber optic cable, a waveguide, a wired communications link, a wireless communication link, etc.).

Figure 12:
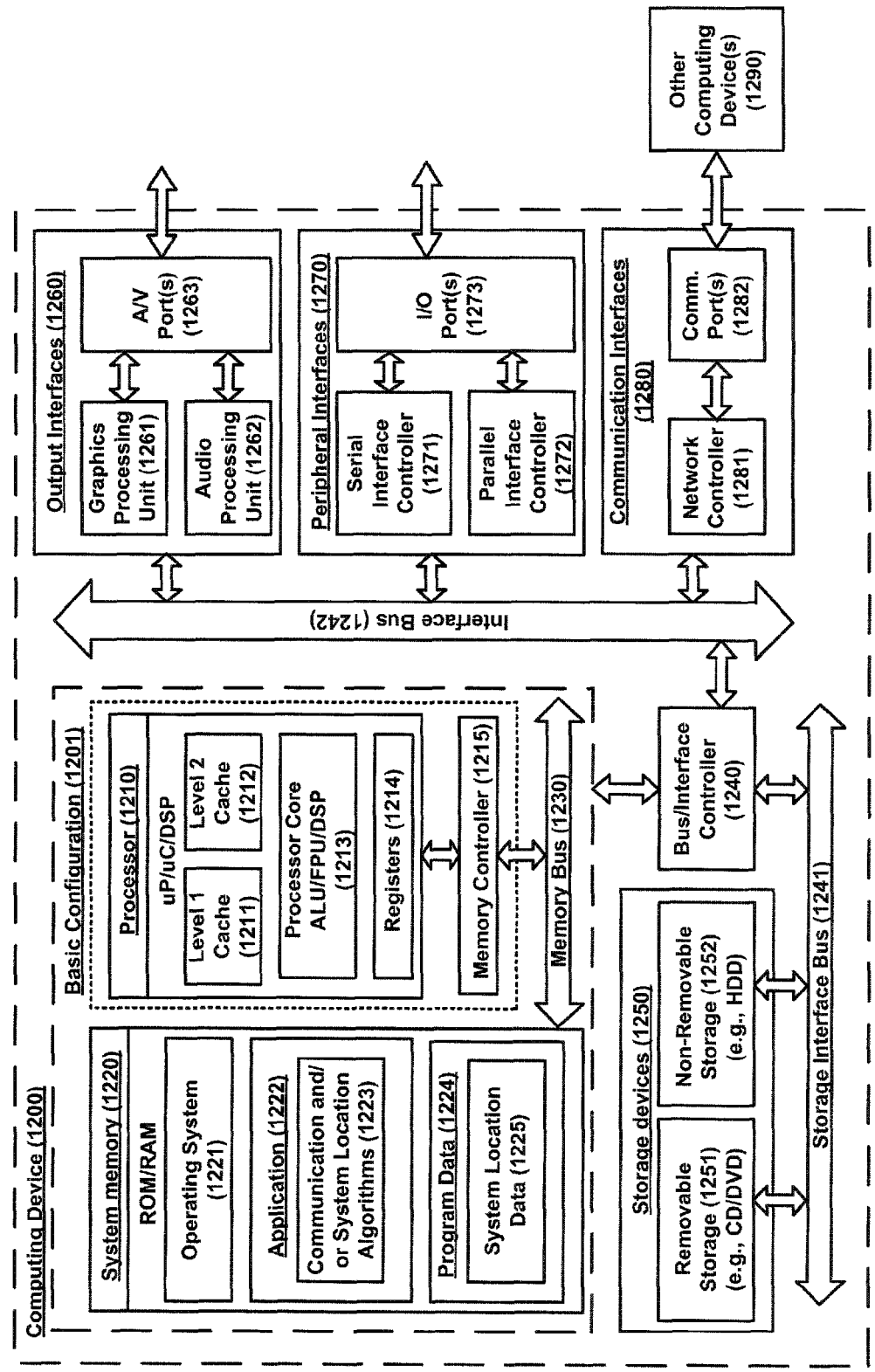
FIG. 12 is a schematic illustrating an exemplary computing device, according to one embodiment of the present disclosure.

FIG. 12 is a block diagram illustrating an exemplary computing device 1200 that is arranged in accordance with the present disclosure. In one example configuration 1201, computing device 1200 may include one or more processors 1210 and system memory 1220. A memory bus 1230 can be used for communicating between the processor 1210 and the system memory 1220.

Depending on the desired configuration, processor 1210 may be of any type including but not limited to a microprocessor (µP), a microcontroller (µC), a digital signal processor (DSP), or any combination thereof. Processor 1210 can include one or more levels of caching, such as a level one (L1) cache 1211 and a level two (L2) cache 1212, a processor core 1213, and registers 1214. The processor core 1213 can include an arithmetic logic unit (ALU), a floating point unit (FPU), a digital signal processing core (DSP Core), or any combination thereof. A memory controller 1215 can also be used with the processor 1210, or in some implementations the memory controller 1215 can be an internal part of the processor 1210.

Depending on the desired configuration, the system memory 1220 may be of any type including but not limited to volatile memory (such as RAM), non-volatile memory (such as ROM, flash memory, etc.) or any combination thereof. System memory 1220 may include an operating system 1221, one or more applications 1222, and program data 1224. Application 1222 may include monitoring and location algorithms that are arranged to perform the functions and/or operations as described herein including the functional blocks and/or operations described with respect to FIGS. 7-10. System Location Data 1224 may include information regarding the location of paramedical devices and/or cardiac arrest monitoring devices. In some example embodiments, application 1222 may be arranged to operate with program data 1224 on an operating system 1221 such that implementations of mobile sampling may be provided as described herein. This described basic configuration is illustrated in FIG. 12 by those components within dashed line 1201.

Computing device 1200 may have additional features or functionality, and additional interfaces to facilitate communications between the basic configuration 1201 and any required devices and interfaces. For example, a bus/interface controller 1240 may be used to facilitate communications between the basic configuration 1201 and one or more data storage devices 1250 via a storage interface bus 1241. The data storage devices 1250 may be removable storage devices 1251, non-removable storage devices 1252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 1220, removable storage 1251 and non-removable storage 1252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1200. Any such computer storage media may be part of device 1200.

Computing device 1200 may also include an interface bus 1242 for facilitating communication from various interface devices (e.g., output interfaces, peripheral interfaces, and communication interfaces) to the basic configuration 1201 via the bus/interface controller 1240. Example output interfaces 1260 may include a graphics processing unit 1261 and an audio processing unit 1262, which may be configured to communicate to various external devices such as a display or speakers via one or more A/V ports 1263. Example peripheral interfaces 1260 may include a serial interface controller 1271 and/or a parallel interface controller 1272, which may be configured to communicate with external devices such as input devices (e.g., keyboard, mouse, pen, voice input device, touch input device, etc.) or other peripheral devices (e.g., printer, scanner, etc.) via one or more I/O ports 1273. An example communication interface 1280 includes a network controller 1281, which may be arranged to facilitate communications with one or more other computing devices 1290 over a network communication via one or more communication ports 1282. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 1200 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 500 may also be implemented as a personal computer including both laptop computer and non-laptop computer configurations. In addition, computing device 500 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

References made in this disclosure to the term "responsive to" or "in response to" are not limited to responsiveness to only a particular feature and/or structure. A feature may also be responsive to another feature and/or structure and also be located within that feature and/or structure. Moreover, when terms or phrases such as "coupled" or "responsive" or "in response to" or "in communication with", etc. are used herein or in the claims that follow, these terms should be interpreted broadly. For example, the phrase "coupled to" may refer to being communicatively, electrically and/or operatively coupled as appropriate for the context in which the phrase is used.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It should also be understood that, the term "optimize" may include maximization and/or minimization. The term "minimization" and/or the like as used herein may include a global minimum, a local minimum, an approximate global minimum, and/or an approximate local minimum. Likewise, it should also be understood that, the term "maximization" and/or the like as used herein may include an global maximum, a local maximum, an approximate global maximum, and/or an approximate local maximum.

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A cardiac arrest monitoring device, comprising:
   a sensor adapted to detect a cardiac rhythm;
   an anomaly detection circuit adapted to detect at least one anomaly based on the detected cardiac rhythm;
   a self-location acquisition unit for acquiring self-location information;
   a paramedical equipment locator adapted to:
      receive a periodically sent message configured to identify a location information corresponding to a paramedical equipment,
      determine a distance corresponding to the paramedical equipment using at least the received location information, and
      determine whether to select the paramedical equipment based at least in part on the determined distance; and
   an output unit configured to output the location information of a selected paramedical equipment;
   wherein the paramedical equipment locator and the output unit are wearable.

2. A device as recited in claim 1, wherein the anomaly detection circuit further comprises a comparison circuit adapted to compare the detected cardiac rhythm with preprogrammed data.

3. A device as recited in claim 2, wherein the preprogrammed data comprises previous cardiac rhythm data of a user of the cardiac monitoring device.

4. A device as recited in claim 1, wherein the paramedical equipment comprises an automated external defibrillator.

5. A device as recited in claim 1, further comprising an alarm unit adapted to generate an alarm response to the anomaly detection circuit detecting the anomaly of the cardiac rhythm.

6. A device as recited in claim 1, wherein the output unit further comprises a video display to plot a location associated with the location information of the selected paramedical equipment on a map.

7. A device as recited in claim 1, wherein the output unit further comprises a video display to graphically display the detected cardiac rhythm.

8. A device as recited in claim 1, further comprising;
   a transmitter for sending the self location information measured by the self-location acquisition unit.

9. A method as recited in claim 1, wherein the periodically sent message is sent from a server.

10. A method as recited in claim 1, wherein the periodically sent message is sent from the paramedical equipment.

* * * * *